(12) United States Patent
Liu et al.

(10) Patent No.: US 9,546,127 B2
(45) Date of Patent: Jan. 17, 2017

(54) PURIFICATION OF CADAVERINE

(71) Applicants: CATHAY R&D CENTER CO., LTD., New District, Shanghai (CN); CATHAY INDUSTRIAL BIOTECH LTD., Grand Cayman (KY)

(72) Inventors: Xiucai Liu, Shanghai (CN); Charlie Liu, Shanghai (CN); Duanfang Dai, Shanghai (CN); Bingbing Qin, Shanghai (CN); Naiqiang Li, Shanghai (CN)

(73) Assignees: CATHAY R&D CENTER CO., LTD., Shanghai (CN); CATHAY INDUSTRIAL BIOTECH LTD., Shanghai (CN)

( * ) Notice: Subject to any disclaimer, the term of this patent is extended or adjusted under 35 U.S.C. 154(b) by 0 days.

(21) Appl. No.: 14/764,101

(22) PCT Filed: Jan. 28, 2013

(86) PCT No.: PCT/CN2013/071044
§ 371 (c)(1),
(2) Date: Jul. 28, 2015

(87) PCT Pub. No.: WO2014/113999
PCT Pub. Date: Jul. 31, 2014

(65) Prior Publication Data
US 2015/0368184 A1    Dec. 24, 2015

(51) Int. Cl.
*C07C 209/84*     (2006.01)
*C12P 13/00*       (2006.01)

(52) U.S. Cl.
CPC ............ *C07C 209/84* (2013.01); *C12P 13/001* (2013.01)

(58) Field of Classification Search
CPC .............................. C07C 209/84; C12P 13/001
See application file for complete search history.

(56) References Cited

U.S. PATENT DOCUMENTS 9,080,190 B2 *   7/2015   Sasaki ................... C12P 13/001

FOREIGN PATENT DOCUMENTS

| WO | 2012077741 A1 | 6/2012 |
| WO | 2012077744 A1 | 6/2012 |

OTHER PUBLICATIONS

International Search Report, PCT/CN2013/071044, Mailed Nov. 7, 2013, 3 pages.

* cited by examiner

*Primary Examiner* — Shailendra Kumar
(74) *Attorney, Agent, or Firm* — Rothwell, Figg, Ernsty & Manbeck, P.C.

(57) ABSTRACT

One aspect of the invention relates to a method for reducing salt content in an aqueous cadaverine salt composition comprising adjusting the pH of the aqueous cadaverine salt composition to provide a first composition comprising an aqueous cadaverine composition and a solid composition, wherein the pH of the aqueous cadaverine composition is at least about 12; and removing the solid composition from the first composition to provide the aqueous cadaverine composition. Another aspect of the invention relates to a method for the purification of cadaverine from an aqueous cadaverine salt composition using the salt-reducing method described herein; and obtaining cadaverine from the aqueous cadaverine composition.

14 Claims, 3 Drawing Sheets

PURIFICATION OF CADAVERINE

CROSS-REFERENCE OF THE RELATED APPLICATION

Figure 1:
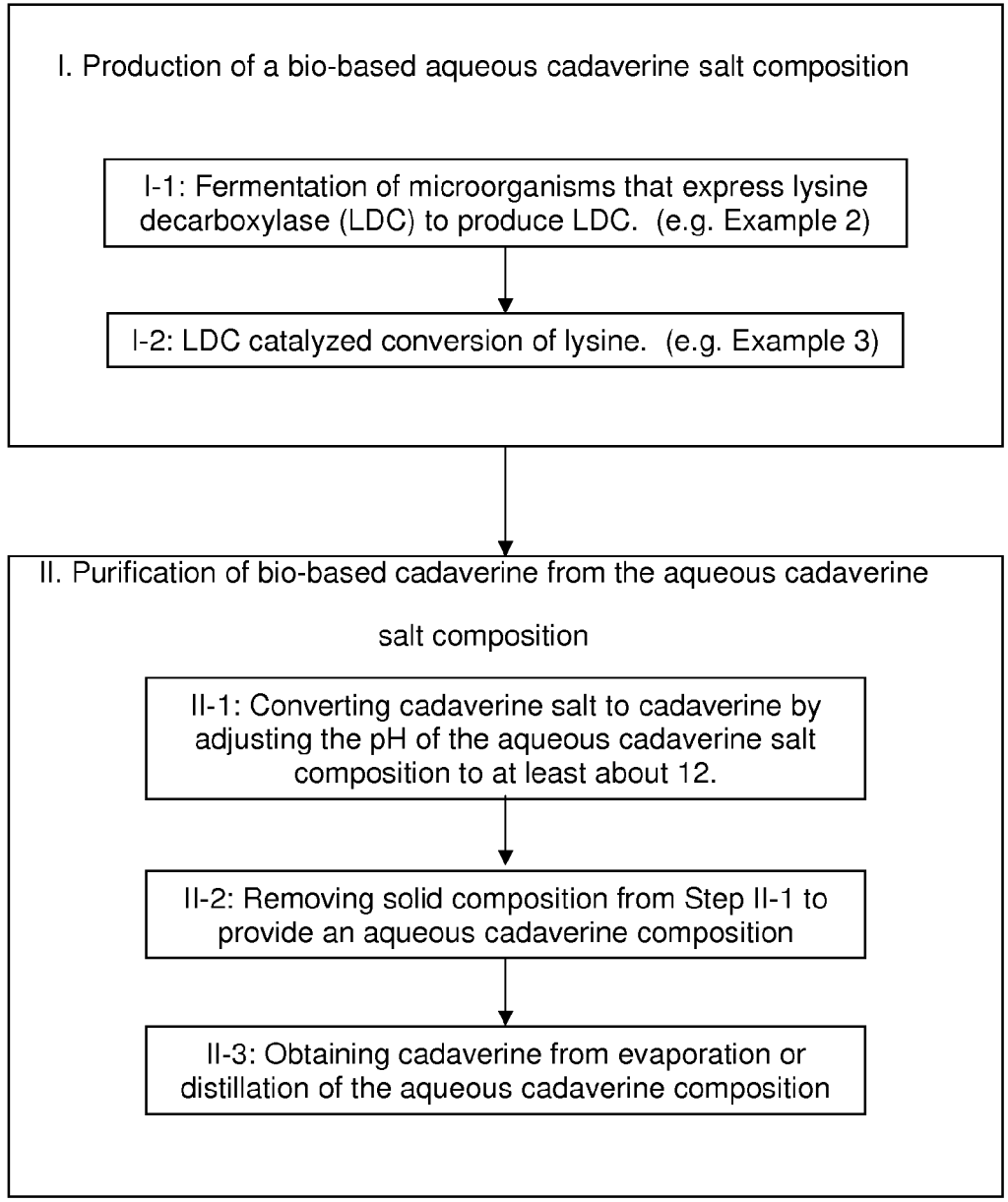

The present application is a 35 U.S.C. §371 National Phase Entry Application of PCT/CN2013/071044, filed 28 Jan. 2013, designating the United States. The application is incorporated herein by reference in its entirety.

TECHNICAL FIELD OF THE INVENTION

The invention relates to methods for purification of cadaverine from cadaverine salt compositions. More specifically, the invention relates to methods for purification of bio-based cadaverine from bio-based productions thereof.

BACKGROUND

Bio-based cadaverine is a valuable platform chemical involved in the production of partially or fully bio-based products, such as partially or fully bio-based Nylon 56 and Nylon 510. Bio-based cadaverine can be synthesized via lysine decarboxylation of lysine in microorganisms. However, currently available purification processes produce bio-based cadaverine with undesired contamination, or require toxic organic solvents in the purification processes.

Thus, there is a need to provide a purification method of bio-based cadaverine to produce bio-based cadaverine of high quality without the use of organic solvent.

SUMMARY OF THE INVENTION

One aspect of the invention relates to a method for reducing salt content in an aqueous cadaverine salt composition comprising:
  a) adjusting the pH of the aqueous cadaverine salt composition to provide a first composition comprising an aqueous cadaverine composition and a solid composition, wherein the pH of the aqueous cadaverine composition is at least about 12; and
  b) removing the solid composition from the first composition of step a) to provide the aqueous cadaverine composition.

Another aspect of the invention relates to a method for the purification of cadaverine from an aqueous cadaverine salt composition, comprising:
  a) adjusting the pH of the aqueous cadaverine salt composition to provide a first composition comprising an aqueous cadaverine composition and a solid composition, wherein the pH of the aqueous cadaverine composition is at least about 12;
  b) removing the solid composition from the first composition of step a) to provide the aqueous cadaverine composition; and
  c) obtaining cadaverine from evaporation or distillation of the aqueous cadaverine composition.

Another aspect of the invention relates to a method for reducing salt content in a production of bio-based cadaverine comprising:
  a-1) providing an aqueous cadaverine salt composition comprising a cadaverine production composition, wherein the cadaverine production composition is obtained from a bio-based cadaverine production process;
  a) adjusting the pH of the aqueous cadaverine salt composition to provide a first composition comprising an aqueous cadaverine composition and a solid composition, wherein the pH of the aqueous cadaverine composition is at least about 12; and
  b) removing the solid composition from the first composition of step a) to provide the aqueous cadaverine composition.

Another aspect of the invention relates to a method for a production of purified bio-based cadaverine comprising:
  a-1) providing an aqueous cadaverine salt composition comprising a cadaverine production composition, wherein the cadaverine production composition is obtained from a bio-based cadaverine production process;
  a) adjusting the pH of the aqueous cadaverine salt composition to provide a first composition comprising an aqueous cadaverine composition and a solid composition, wherein the pH of the aqueous cadaverine composition is at least about 12;
  b) removing the solid composition from the first composition of step a) to provide the aqueous cadaverine composition; and
  c) obtaining purified bio-based cadaverine from evaporation or distillation of the aqueous cadaverine composition.

BRIEF DESCRIPTION OF THE FIGURES AND DRAWINGS

FIG. 1: A flow chart showing an embodiment according to a method disclosed herein.

Figure 2:
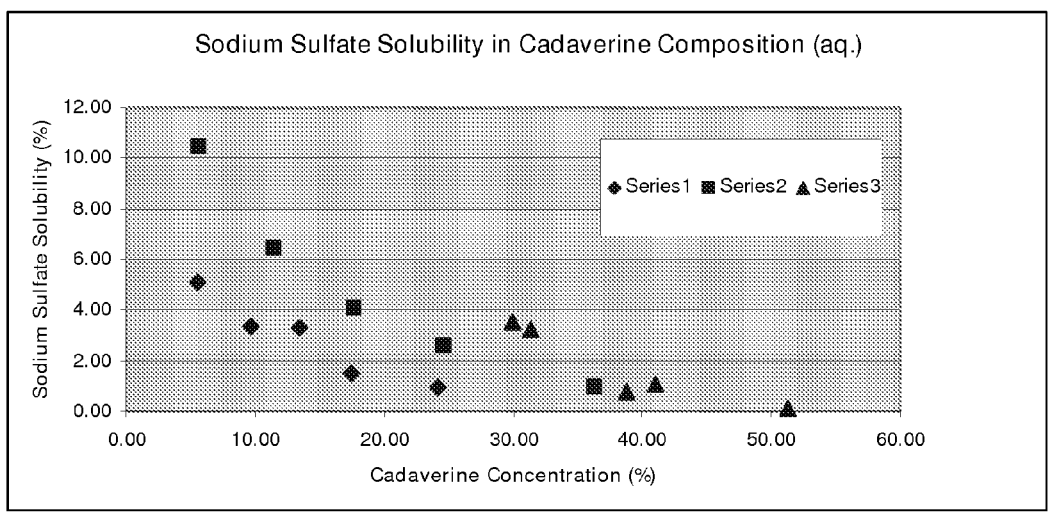

FIG. 2: Sodium sulfate solubility curves in cadaverine composition (aq.) at 5° C. (Series 1); 18° C. (Series 2); and 65° C. (Series 3).

Figure 3:
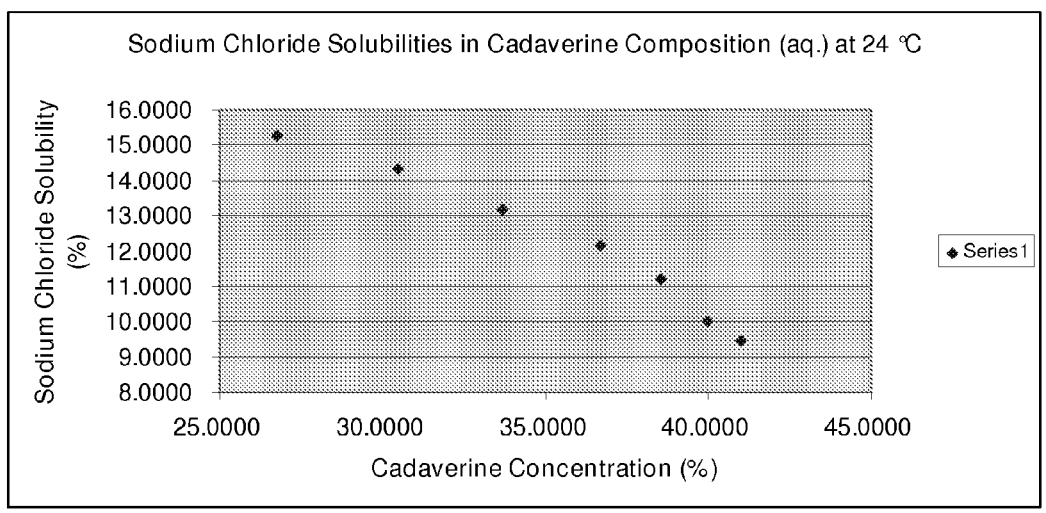

FIG. 3: Sodium chloride solubility curve in cadaverine composition (aq.) at 24° C. (Series 1).

DETAILED DESCRIPTION OF THE INVENTION

Bio-based cadaverine production can be produced via fermentation process or enzymatic conversion of lysine (e.g. as shown in Block I, FIG. 1). As used herein, a "bio-based" compound means the compound is considered bio-based under Standard ASTM D6866. In the fermentation process, microorganisms that produce lysine and express lysine decarboxylase (LDC) are fermented to produce cadaverine. In the enzymatic conversion of lysine, lysine/lysine salt can be converted to cadaverine catalyzed by LDC (e.g. Block I-2, FIG. 1; and Example 3). In one embodiment, the LDC is produced by fermenting microorganisms that express lysine decarboxylase (LDC) (e.g. Block I-1, FIG. 1; and also Example 2). Cadaverine has a relatively low boiling point and is relatively easy to evaporate/distil. However, cadaverine is protonated under the desired working pH of LDC, and forms one or more cadaverine salts that are difficult to distil. Thus, in one embodiment, one or more bases are added into an aqueous cadaverine salt composition to convert the cadaverine salt to cadaverine (e.g. Block II-1, FIG. 1). The obtained composition comprises an aqueous cadaverine composition and a solid composition. The aqueous cadaverine composition comprises cadaverine and other water soluble components (e.g. one or more inorganic salts). The final pH of the aqueous composition is about 12 or higher such that the protonated cadaverine is substantially converted to cadaverine. The solid composition comprises one or more inorganic salts. The inorganic salts are involatile and may significantly interfere with the evaporation/distillation of cadaverine from the aqueous cadaverine composition, particularly as water is removed during the evaporation/distillation. As used herein, an evaporation/distillation composition is a heated composition during the evaporation/distillation. In a method described herein, removal of the solid composition from the aqueous cadaverine composition (e.g. Block II-2, FIG. 1) allows removal of a significant amount of the inorganic salts from the evaporation/distillation composition for better recovery of cadaverine via evaporation/distillation (e.g. Block II-3, FIG. 1).

One aspect of the invention relates to a method for reducing salt content in an aqueous cadaverine salt composition comprising:

a) adjusting the pH of the aqueous cadaverine salt composition to provide a first composition comprising an aqueous cadaverine composition and a solid composition, wherein the pH of the aqueous cadaverine composition is at least about 12; and b) removing the solid composition from the first composition of step a) to provide the aqueous cadaverine composition.

Another aspect of the invention relates to a method for the purification of cadaverine from an aqueous cadaverine salt composition, comprising:

a) adjusting the pH of the aqueous cadaverine salt composition to provide a first composition comprising an aqueous cadaverine composition and a solid composition, wherein the pH of the aqueous cadaverine composition is at least about 12;

b) removing the solid composition from the first composition of step a) to provide the aqueous cadaverine composition; and c) obtaining cadaverine from evaporation or distillation of the aqueous cadaverine composition.

Another aspect of the invention relates to a method for reducing salt content in a production of bio-based cadaverine comprising:

a-1) providing an aqueous cadaverine salt composition comprising a cadaverine production composition, wherein the cadaverine production composition is obtained from a bio-based cadaverine production process;

a) adjusting the pH of the aqueous cadaverine salt composition to provide a first composition comprising an aqueous cadaverine composition and a solid composition, wherein the pH of the aqueous cadaverine composition is at least about 12; and b) removing the solid composition from the first composition of step a) to provide the aqueous cadaverine composition.

Another aspect of the invention relates to a method for a production of purified bio-based cadaverine comprising:

a-1) providing an aqueous cadaverine salt composition comprising a cadaverine production composition, wherein the cadaverine production composition is obtained from a bio-based cadaverine production process;

a) adjusting the pH of the aqueous cadaverine salt composition to provide a first composition comprising an aqueous cadaverine composition and a solid composition, wherein the pH of the aqueous cadaverine composition is at least about 12;

b) removing the solid composition from the first composition of step a) to provide the aqueous cadaverine composition; and c) obtaining purified bio-based cadaverine from evaporation or distillation of the aqueous cadaverine composition.

I) Aqueous Cadaverine Salt Compositions

An aqueous cadaverine salt composition comprises a cadaverine salt and/or a fully or partially protonated cadaverine. In one embodiment, the pH of the aqueous cadaverine salt composition is no more than about 12, no more than about 11, no more than about 10 or lower, no more than about 9, or about 7 to about 8. In another embodiment, the cadaverine salt is formed from cadaverine and one or more acids selected from the group consisting of organic acid, inorganic acids, and any combinations thereof. Examples of the inorganic acids include, without limitation, hydrochloride, sulfuric acid, carbonic acid, and phosphoric acid. Examples of the organic acids include, without limitation, hexdicarboxylic acid, and acetic acid. In another embodiment, the aqueous cadaverine salt composition comprises acid anions. Examples of the acid anions include, without limitation, $Cl^-$, $SO_4^{2-}$, $^-OOC(CH_2)_3COO^-$, $CH_3COO^-$, $CO_3^{2-}$, $PO_4^{3-}$, and any combinations thereof. As used herein, cadaverine chloride is cadaverine chloride, cadaverine dichloride, or a mixture thereof.

In another embodiment, the aqueous cadaverine salt composition comprises a cadaverine production composition obtained from a bio-based cadaverine production process.

Examples of the bio-based cadaverine production process include, without limitation, fermentative production and in vitro enzymatic production. In certain embodiments, the cadaverine production compositions obtained from the bio-based cadaverine production have a pH of no more than about 12, no more than about 11, no more than about 10 or lower, no more than about 9, or about 7 to about 8, wherein most of the cadaverine in the cadaverine production composition is presented in a salt form.

a) Enzymatic Production of Bio-Based Cadaverine

In one embodiment, the aqueous cadaverine salt composition comprises a cadaverine production composition obtained from an enzymatic bio-based cadaverine production process. The enzymatic bio-based cadaverine production process comprises converting lysine and/or a lysine salt (lysine/lysine salt) to cadaverine in the presence of lysine decarboxylase (LDC). In one example, the production is carried out in an aqueous media.

i) Lysine/Lysine Salt

The lysine salts are salts formed from lysine and one or more acids selected from the group consisting of inorganic acids, organic acids, and any combinations thereof. In certain embodiments, the lysine salts are one or more lysine/inorganic acid salts. Examples of lysine/inorganic acid salts include, without limitation, lysine hydrochloride, lysine sulfate and any combinations thereof.

Lysine/lysine salt can be prepared from any suitable fermentative production, and the lysine fermentation broth obtained therefrom can be used in the enzymatic production of bio-based cadaverine. In one embodiment, the lysine fermentation broth comprises an aqueous lysine sulfate solution. In another embodiment, the lysine fermentation broth is further processed before use in the enzymatic bio-based cadaverine production. For example, the lysine fermentation broth can be further processed (e.g. via filtration, centrifuge or membrane-filtration) to remove impurities (e.g. microbes) and provide the aqueous lysine salt solution. In one example, an aqueous lysine sulfate solution is obtained from the lysine fermentation process. The aqueous lysine sulfate solution is further processed using ion-exchange resin, wherein the eluate is neutralized with hydrochloride acid to provide aqueous lysine hydrochloride solution. In another example the lysine fermentation broth is decolored with activated carbon and filtered to provide aqueous lysine sulfate solution.

Commercially available lysine/lysine salt products (e.g. lysine hydrochloride) may also be used in the enzymatic bio-based cadaverine production. In one embodiment, a lysine fermentation broth obtained from the fermentation process is used in the enzymatic bio-based cadaverine production.

Any microbes suitable for lysine fermentation can be used herein. Examples of the microbes include, without limitation, wild-type strains, induced mutant strains, and/or recombinant strains. Examples of the strains include, without limitation, *Corynebacterium* strains (e.g. *C. glutamicum*, *C. pekinense*, and *C. crenatum*), and *Brebvibacterium* strains (e.g. *B. lactofermentum* and *B. flavum*).

The lysine fermentation process is carried out in a medium. Such a medium can be any medium suitable for the fermentation. For example, the medium may contain carbon sources and non-carbon nutrient sources. Examples of the carbon sources include, without limitation, sugar (e.g. carbohydrates such as glucose and fructose), oil and/or fat, a fatty acid, and/or derivatives thereof. The oil and fat may contain saturated and/or unsaturated fatty acids having 10 or more carbon atoms, e.g. coconut oil, palm oil, palm kernel oil, and the like. The fatty acid may be a saturated and/or unsaturated fatty acid, e.g. hexanoic acid, octanoic acid, decanoic acid, lauric acid, oleic acid, palmitic acid, linoleic acid, linolenic acid, myristic acid, and the like. Examples of the derivatives of a fatty acid include, without limitation, esters and salts thereof. Examples of the non-carbon sources include, without limitation, nitrogen sources (e.g. beef extract, yeast extract and corn steep liquor), inorganic salts, and other organic nutrient sources.

Examples of the nitrogen source may comprise ammonia, ammonium salts (e.g. ammonium chloride, ammonium sulfate and ammonium phosphate), tryptone, meat extract, yeast extract, and the like. Examples of the inorganic salts include, without limitation, potassium dihydrogen phosphate, dipotassium hydrogen phosphate, magnesium phosphate, magnesium sulfate, sodium chloride, and the like. Examples of the other organic nutrient source include, without limitation, amino acids (e.g. glycine, alanine, serine, threonine and proline), vitamins (e.g. vitamin B1, vitamin B12 and vitamin C), and the like. The composition of the medium may be adjusted and optimized according to the type of strains and the product of the fermentation.

The fermentation may be carried out at any temperature at which the cells can grow, and preferably at about 20° C. to about 40° C., or about 35° C. The culture period may be about 1 day, about 2 days, about 3 days, about 4 days, about 5 days, about 6 days, about 7 days, about 8 days, about 9 days, or about 10 days.

ii) LDC

LDC is an enzyme that can convert lysine to 1,5-cadaverine. LDC may be prepared from any suitable fermentative production, and the LDC fermentation broth obtained therefrom can be used directly in the enzymatic production of bio-based cadaverine. In certain embodiments, the LDC fermentation broth may be further processed before use in the cadaverine enzymatic production. For example, the LDC fermentation broth may be centrifuged, filtered, or otherwise processed or further purified to provide processed or purified LDC compositions. Examples of the processed/purified LDC compositions include, without limitation, LDC fermentation cells and/or fragments thereof; LDC supernatant obtained from centrifuging or filtering the LDC fermentation broth; LDC supernatant obtained from removal of cells by centrifuge or filtration of the LDC fermentation broth; purified LDC and compositions thereof; and any combinations of more than one type of LDCs.

Any microbes suitable for LDC fermentation can be used herein. Examples of the microbes include, without limitation, wild-type strains, induced mutant strains, and/or recombinant strains. Examples of the strains include, without limitation, induced mutant *Escherichia coli*, induced mutant *Hafnia alvei*, and recombinant *Escherichia coli*, and recombinant *Hafnia alvei* (e.g. the recombinant *Hafnia alvei* disclosed in Chinese application No. 201210177392.X).

The LDC fermentation process is carried out in a medium. Such a medium can be any medium suitable for the fermentation. For example, the medium can be the same as or similar to the medium used in the lysine fermentation process, which contains carbon sources and non-carbon nutrient sources as described supra, and is optimized for the LDC fermentation.

The fermentation may be carried out at any temperature at which the cells can grow, and preferably at about 20° C. to about 40° C., or about 35° C. The culture period may be about 1 day, about 2 days, about 3 days, about 4 days, about 5 days, about 6 days, about 7 days, about 8 days, about 9 days, or about 10 days.

iii) Lysine Decarboxylation (LDCN) Reaction

Any suitable enzymatic production of bio-based cadaverine from lysine/lysine salt can be used herein. In an LDCN reaction, the substrate is lysine/lysine salt as described supra, and the enzyme is LDC as described supra. The reaction temperature may be from about 20° C. to about 60° C. The desired reaction pH is a pH that is suitable for the enzymatic conversion, and depends on the LDC used in the LDCN reaction. In certain embodiments, the suitable reaction pH may range from about 5 to about 8.

In one embodiment, an acid is added in the LDCN reaction to maintain the reaction pH within the suitable range. In one example, the acid is added in the lysine/lysine salt solution before adding LDC to adjust the pH to a suitable pH, then LDC is added to facilitate the conversion of lysine to cadaverine. In another example, the acid is added into the reaction after LDC is mixed with the lysine/lysine salt solution. Examples of suitable acids include, without limitation, inorganic acid (e.g. HCl, sulfuric acid, and any combinations thereof), and acidic gas (e.g. $CO_2$).

In another embodiment, a buffer is used in the LDCN reaction to maintain the pH within the suitable range to optimize the conversion yield. Examples of the buffers include, without limitation, common buffers used in the working range of LDC, e.g. 7 part 0.2 mol/L acetic acid plus 3 part 0.2 mol/L sodium acetate solution.

In another embodiment, the starting pH and the ending pH of the LDCN reaction are within the suitable pH range for the enzymatic conversion, and additional acid or other substance may or may not be added into the reaction for pH control.

In certain embodiments, the substrate and enzyme may be added in the reaction at more than one time, respectively. The manner of addition of enzyme and/or substrate can be adjusted to optimize the conversion of the enzymatic conversion.

In certain embodiments, cell immobilization technology is applied on LDC to improve the reaction yield. Any suitable cell immobilization method can be used, e.g. embedding method (e.g. calcium alginate embedding method).

In certain embodiments, other additives facilitating the enzymatic conversion may be present in the LDCN reaction mixture. Examples of such additives include, without limitation, inorganic salts and vitamins.

II) Adjusting the PH of an Aqueous Cadaverine Salt Composition To Provide a First COMPOSITION COMPRISING AN AQUEOUS CADAVERINE SOLUTION HAVING A PH OF AT LEAST ABOUT 12.

The aqueous cadaverine salt composition is as described supra. In one embodiment, the pH of the aqueous cadaverine salt composition is no more than about 12, no more than about 11, no more than about 10 or lower, no more than about 9, or about 7 to about 8.

In another embodiment, the aqueous cadaverine salt composition comprises a cadaverine production composition obtained from a LDCN reaction as described supra.

The pH of an aqueous cadaverine composition depends on the cadaverine concentration and the temperature (e.g. Table 1 of Example 5).

The pH of the aqueous cadaverine salt composition can be adjusted by adding one or more inorganic bases therein. A cadaverine salt reacts with the one or more inorganic bases to provide cadaverine and the corresponding one or more inorganic salts. In certain embodiments, the one or more inorganic salts cannot completely dissolve in the aqueous solution, and are precipitated from the aqueous solution as a solid composition. Thus, the first composition of step a) comprises a solid composition and an aqueous solution, wherein the solid composition comprises the one or more inorganic salts, and the aqueous solution comprises cadaverine and the one or more inorganic salts.

Examples of the one or more inorganic bases include, without limitation, hydroxides, such as alkaline metal hydroxides (e.g. NaOH, KOH, and a mixture thereof), alkaline earth metal hydroxides (e.g. $Mg(OH)_2$, $Ca(OH)_2$, and a mixture thereof), and basic salts thereof (e.g. sodium phosphate, potassium phosphate, sodium carbonate, potassium carbonate, and a mixture thereof). The one or more bases may be added into the aqueous cadaverine salt composition at substantially the same time or at different time. When more than one base is added, the different bases may be added as one or more mixtures or separately. In certain embodiments, the base mixtures may be a mixture of one or more strong bases and one or more weak bases. Examples of the base mixtures include, without limitation, a mixture of sodium phosphate and sodium hydroxide, and a mixture of sodium carbonate, sodium hydroxide and potassium hydroxide. In certain embodiments, the base mixtures may be a mixture of one or more strong bases. Examples of the base mixtures include, without limitation, a mixture of sodium hydroxide and potassium hydroxide.

Scheme 1 illustrates an example of the reaction wherein the cadaverine salt is a hydrochloride salt and the base is NaOH:

Scheme 1

$[NH_3(CH_2)_5NH_3]Cl_2 + 2NaOH \longrightarrow NH_2(CH_2)_5NH_2 + 2NaCl + 2H_2O$ A person of ordinary skill in the art would readily understand and appreciate other reactions wherein cadaverine and one or more inorganic salts are produced from reactions between one or more specific cadaverine salts and one or more specific bases. Examples of the one or more inorganic salts include, without limitation, sodium sulfate, sodium carbonate, NaCl, potassium sulfate, and KCl.

The one or more bases may be added as solid and/or as solution (e.g. aqueous solution).

The amounts of the one or more bases added depend on the amount of cadaverine in the aqueous cadaverine salt composition. The amounts of the one or more bases are suitable when a substantial amount of the cadaverine salt is converted to cadaverine. In certain embodiments, the pH of the resulting aqueous solution is no less than about 12, no less than about 13, no less than about 13.3, or no less than about 13.5.

The one or more bases may be added to and/or reacted with the aqueous cadaverine salt composition at any temperature that allows the production of cadaverine from the cadaverine salt. In general, the higher the reaction temperature, the faster the reaction runs.

In one embodiment, the base is an aqueous sodium hydroxide solution, the aqueous cadaverine salt composition is an aqueous cadaverine sulfate solution, the base is added at about 60° C. and the reaction almost completes immediately after the addition of the base, sodium hydroxide.

In another embodiment, the methods disclosed herein further comprise adding the one or more bases at a first temperature, and optionally reacting the reaction at a second temperature for about a first time. The first and the second temperatures can be the same or different. The first and/or the second temperature can be about 10° C. to about 80° C., about 40° C. to about 80° C., about 10° C., about 40° C., about 60° C., about 70° C., or about 80° C. The first reaction time is the time required to substantially convert amount of the cadaverine salt to cadaverine (i.e. remaining cadaverine salt concentration is no more than about 5%). A person of ordinary skill in the art would understand and appreciate how to determine the first reaction time. In certain embodiment, the first reaction time is about 0.01 to about 2 hours.

As used herein, unless otherwise specified, all concentrations are concentrations by weight (w/w).

In general, the higher the cadaverine concentration in an aqueous solution, the lower the solubility of an inorganic salt therein is. (See, FIGS. 1 and 2, the solubility curves of NaCl and $Na_2SO_4$ in an aqueous cadaverine composition at different cadaverine concentrations, respectively.)

Although any concentration of the aqueous cadaverine salt composition may be suitable for this method, in certain embodiments, the solid composition is removed from the aqueous cadaverine composition wherein the cadaverine concentration of the aqueous cadaverine composition is about 5% or higher, about 10% or higher, about 15% or higher, about 20% or higher, or about 30% or higher. In certain embodiments, optionally, the methods disclosed herein further comprise:

a-11) concentrating the aqueous cadaverine salt composition before the addition of the one or more bases; and/or optionally a-12) concentrating the aqueous cadaverine salt composition/base reaction after the addition of the one or more bases; and/or optionally a-13) concentrating the aqueous cadaverine salt composition/base reaction during the addition of the one or more bases;

such that the cadaverine concentration of the aqueous cadaverine composition of step a) is about 5% or higher, about 10% or higher, about 15% or higher, about 20% or higher, or about 30% or higher.

In one embodiment, the aqueous cadaverine salt composition is a cadaverine sulfate solution obtained from a LDCN reaction; the base is NaOH. A cadaverine/$Na_2SO_4$ mixture is provided from the reaction of cadaverine sulfate and NaOH. When the cadaverine concentration of the aqueous solution of the cadaverine/Na$_2$SO$_4$ mixture is about 17% or higher, about 80% or more of the Na$_2$SO$_4$ is precipitated from the aqueous solution.

III) Removing the Solid Composition from the First Composition of Step A) to provide the Aqueous Cadaverine Composition The solid composition may be separated from the first composition of step a) by any method suitable to separate solid from liquid, e.g. centrifuge, and filtration.

In certain embodiments, the acid anion content of the aqueous cadaverine composition obtained from step b) is no more than about 70%, no more than about 50%, or no more than about 30% of that of the cadaverine salt composition.

In general, the lower the solution temperature, the lower the solubility of an inorganic salt therein is. As shown in FIG. 2, at about the same cadaverine concentration (e.g. about 20%), sodium sulfate solubility at a higher temperature (18° C.) is more than that at a lower temperature (5° C.). FIG. 2 also shows that when the cadaverine concentration is relatively high (e.g. about 30% or higher, or about 40% or higher), sodium sulfate solubility is low even at a relatively high temperature (e.g. 65° C.).

In certain embodiments, the methods disclosed herein optionally further comprise:

a-21) maintaining the first composition at a third temperature for a second time before the performance of step b).

The third temperature can be from about 2° C. to about 80° C., about 2° C., about 4° C., about 5° C., about 10° C., about 15° C., about 35° C., about 38° C., about 40° C., about 50° C., or about 65° C. In certain embodiments, the third temperature is not higher than the first and/or the second temperature described supra. In certain embodiments, the third temperature is lower than the second temperature to facilitate the precipitation of the one or more inorganic salt from the aqueous solution of step a).

In certain embodiments, step b) disclosed herein comprises:

b-1) filtering/centrifuging the first composition to provide a solid and a filtrate/supernatant;

b-2) rinsing the solid with an aqueous salt solution and filtering/centrifuging the obtained mixture to provide another solid and another filtrate/supernatant;

b-3) optionally repeating step b-2) until the solid obtained is substantially free of cadaverine; and b-4) combining the filtrates/supernatants obtained from steps b-1), b-2) and b-3) to provide the aqueous cadaverine composition to be further processed in step c).

In certain embodiments, the aqueous salt solution used in the rinse of each step b-2) can be the same or different. Examples of such aqueous salt solution include, without limitation, saturated aqueous salt solutions (e.g. NaCl saturated aqueous solution, and sodium sulfate saturated aqueous solution).

In certain embodiments, the temperature at which steps b-1) and b-2) are performed can be the same or different, and can be the third temperature described above.

In one embodiment, the aqueous cadaverine salt composition is cadaverine sulfate, the base is NaOH, and the first and the second temperatures are 60° C. When the third temperature is 35° C., in the obtained aqueous solution, the cadaverine concentration is about 20%, and the concentration of SO$_4^{2-}$ is about 3% or lower.

In another embodiment, the aqueous cadaverine salt composition is cadaverine sulfate, the base is NaOH, the first and the second temperatures are 10° C. In the obtained aqueous solution, the cadaverine concentration of the aqueous solution of resulting reaction is about 10%. When the third temperature is about 2° C., and the second time is about 1 hour, the concentration of SO$_4^{2-}$ is about 3.5% or lower.

In another embodiment, the aqueous cadaverine salt composition is cadaverine sulfate, the base is NaOH, the first and the second temperatures are 80° C. The third temperature is 40° C., and the second time is about 1 hour. In the obtained aqueous solution, the cadaverine concentration of the aqueous solution of resulting reaction is about 30%, and the concentration of SO$_4^{2-}$ is about 2% or lower.

Iv) Obtaining Cadaverine from Evaporation Or Distillation of the Aqueous Cadaverine Composition The aqueous cadaverine composition obtained from step b) comprises water, cadaverine, and impurities (e.g. one or more inorganic salts and other organic materials).

Cadaverine can be evaporated/distilled from the aqueous cadaverine composition via any suitable evaporation/distillation method/equipments. Examples include, without limitation, multi-effect evaporator, and fractional distillation/rectification equipments.

In certain embodiments, the aqueous cadaverine composition is evaporated/distilled twice or more to provide cadaverine with higher purity (e.g. at least about 95%, at least about 98%, at least about 99%, at least about 99.5%, or at least about 99.8%). Each evaporation/distillation may be carried out at reduced pressure or ambient pressure, although reduced pressure is preferred. The first distillate obtained from the first evaporation/distillation comprises cadaverine and water. Then the first distillate (cadaverine/water mixture) is further distilled to provide cadaverine with higher purity. Each evaporation/distillation process can be accomplished using any suitable method/equipment (e.g. evaporation, multi-effect evaporation, and rectification).

In one embodiment, the heating temperature is about 50° C. to about 250° C., about 50° C. to about 80° C., about 70° C. to about 185° C., about 70° C. to about 120° C., about 80° C. to about 120° C., about 80° C. to about 180° C. The distillation pressure is about 5 kg or less (gauge pressure), a pressure lower than the ambient pressure (gauge pressure), about 0.02 MPa or lower (absolute pressure), about 0.085 MPa or lower (absolute pressure), about 0.095 MPa or lower (absolute pressure), or about 0.096 MPa or lower (absolute pressure).

The heating temperature depends on the distillation pressure. In one embodiment, the purified cadaverine is obtained from heating the aqueous cadaverine composition with an oil bath (180° C.) under vacuum (−0.085 MPa), with an oil bath (135° C.) under vacuum (−0.096 MPa), or with an oil bath (120° C.) under vacuum (−0.095 MPa).

V) Advantages

The methods disclosed herein remove a significant amount of inorganic salt from an aqueous cadaverine salt composition without organic solvent extraction. The reduced salt content in the cadaverine evaporation/distillation composition provides an evaporation/distillation composition that is easier to heat which facilitates a more effective and efficient cadaverine evaporation/distillation.

In certain embodiments, the methods disclosed herein significantly increase the cadaverine recovery yield. In one example (Example 10), an aqueous cadaverine salt composition is purified using a method disclosed (a first method) herein and a second method that is substantially the same as the first method except that the second method does not include the solid-removal treatment of step b). Both methods use substantially similar distillation condition and distillation time. The cadaverine recovery yield of the first method is about 93.26%, which is significantly higher than that of the second method, about 77.5%. In another example (e.g.

Example 4), an aqueous cadaverine salt composition is converted to an aqueous cadaverine composition, then the aqueous cadaverine composition is extracted with an organic solvent before cadaverine distillation. Significant amount of impurities are still left in the evaporation/distillation composition, which interfere the cadaverine distillation and lowered the cadaverine recovery yield (62.35%).

In certain embodiments, the methods disclosed herein significantly reduce the distillation time and/or the distillation temperature required in the cadaverine evaporation/distillation.

VI) EXAMPLES

The following description provides specific details for a thorough understanding of, and enabling description for, embodiments of the disclosure. However, one skilled in the art will understand that the disclosure may be practiced without these details. In other instances, well-known structures and functions have not been shown or described in detail to avoid unnecessarily obscuring the description of the embodiments of the disclosure.

Lysine was detected according to the standard method for determination of food additive L-lysine hydrochloride (GB10794-2009). Sulfate ion was detected according to the standard method for determination of industrial anhydrous sodium sulfate (GB6009-92). Other ions were detected by ion chromatography. Cadaverine was detected according to the cadaverine characteristic absorption near 2.5 ppm in NMR spectrum. DMSO was used as the internal standard. Cadaverine salt compositions were also characterized by cadaverine concentration by adjusting the pH of the test sample to at least about 14 before NMR spectrums were taken.

Bio-based aqueous cadaverine salt compositions were prepared according to the methods disclosed in Examples 1, 2, and 3. Other approaches may also be used in transformation of lysine into cadaverine by microorganisms. (See, e.g., "Study on the transformation of 1-lysine into cadaverine by microorganism," Jing Zhu, Master Thesis, Tianjin University of Science and Technology, March, 2009). Example 4 describes a conventional extraction purification of cadaverine from a cadaverine salt composition. Example 5 shows the changes of pH of cadaverine aqueous solution when the cadaverine concentration changes. Examples 6 and 7 show the effective salt reduction from a few embodiments according to the methods disclosed herein. Example 8 is the measurement of the solubilities of NaCl and $Na_2SO_4$ in cadaverine aqueous solutions of different cadaverine concentrations. Example 9 shows the effective cadaverine purification from an aqueous cadaverine sulfate composition prepared from purified cadaverine (purity 95.00%). Examples 10-11 include cadaverine purification from bio-based cadaverine salt compositions (e.g. cadaverine chloride or cadaverine sulfate) according to the cadaverine purification method disclosed herein, and cadaverine purification from similar bio-based cadaverine salt compositions without the salt reduction step (i.e. step b) recited in the methods disclosed herein.

Example 1

Preparation of a Lysine Fermentation Broth (1) LB Medium Slants:
LB medium slants were prepared using LB medium containing tryptone 1%, yeast extract 0.5%, and NaCl 1%, pH 7.2.

(2) Primary Seed Culture Medium (Shake Flask Seed Culture Medium)
A *Corynebacterium* culture expressing lysine was grown on the LB medium slants, and transferred into a 500 mL seed flask containing the 200 mL liquid medium (liquid broth medium containing beef extract 1%, tryptone 1%, yeast extract 0.5%, and NaCl 0.5%, pH 7.0), then cultured at 33° C. on 200 rmp shaking bed for 10-15 hours.

(3) Lysine Fermentation
A fermentation medium (5 L) was added to a 10 L fermentor. Then the seed liquid prepared above was transferred into the fermentor for fermentation. The fermentation medium contained: glucose 1.5%, molasses 0.2%, corn steep liquor 0.06%, soybean meal hydrolysate 0.05%, ammonium sulfate 0.2%, dipotassium hydrogen phosphate 0.01%, and magnesium sulfate 0.005%. After sterilization at 121° C. for 20 minutes, the fermentor was rotated at 400-500 rpm at 31-33° C. for fermentation, the amount of air introduced to the fermentor was controlled at 0.5-1.2 vvm, DO>20%. In the process, a stream sugar was added to control the sugar concentration to about 0.5%; a stream of ammonium sulfate was added to control the ammonia concentration to about 0.1%; and a stream of ammonia was added to control the pH at about 6.5-6.8. Meanwhile, bubble enemy (glycerol polyoxypropylene polyoxyethylene ethers) was added to control bubbles in the fermentation process. The whole fermentation process lasted for about 41 hours. The tank liquid released had a lysine concentration of about 12%.

(4) Work-Up of the Lysine Fermentation Broth
The lysine fermentation broth was optionally further processed (e.g. filtered, centrifuged, and/or filtered through membrane) to remove the cells to obtain a clear liquid.

Example 2

Preparation of Lysine Decarboxylase (LDC)

(1) Seeds and Fermentation Medium:
Seed culture medium (g/L): Tryptone 10, beef extract 5, NaCl 5, corn steep liquor, 5, pH 7.2. A wild *Hafnia alvei* strain (Hafnia alvei 1.1009 from CGMCC, http://www.cgmcc.net/index.php/Contents/show/id/460) expressing LDC was grown on slant, transferred to a triangle flask containing 30 mL seed medium, and cultured at 35° C. with shaking at 170 R/min for 15 hours.

(2) Culture Conditions
Fermentation medium (g/L): glucose 18, yeast extract 20, corn steep liquor 36.6, $MgSO_4$ 0.3, $KH_2PO_4$ 0.1, NaCl 3, L-lysine 5, vitamin $B_6$ 1, and pH 6.5-7.0.

10% seed was transferred into a 250 mL flask containing 100 mL fermentation medium. In the cell growth phase, the temperature was controlled at 35° C. and the cells were cultured on a rotary shaker 200 r/min oscillation for 13 hours; then cultured statically for 5 hours. The obtained LDC fermentation broth was used directly in LDC catalyzed conversion of lysine or centrifuged to obtain wet cells.

Example 3

LDC Catalyzed Conversion of Lysine (1) Enzymatic Conversion of Lysine Hydrochloride
100 L LDC fermentation broth (Example 2) was added in a 250 L reactor, acetic acid and sodium acetate were added to the reaction to final molar concentrations of 0.2 mol/L, respectively. Commercially available lysine hydrochloride was added to the reaction to control the lysine concentration at 3 g/L, and Tween-80 (total 0.15 kg) was added to the reaction. The reaction was stirred at 35° C. The reaction was complete within about 5 hours, with a lysine molar conversion rate of about 98%. The enzymatic conversion solution was concentrated to obtain a cadaverine salt solution (about 5%), which was ready for optional further processing.

(2) Enzymatic Conversion of Lysine Sulfate

100 L LDC fermentation broth (Example 2) was added in a 250 L reactor, acetic acid and sodium acetate were added to the reaction to inal molar concentrations of 0.2 mol/L, respectively. Commercially available lysine sulfate (65%) was added to the reaction to control the lysine concentration at 3 g/L, and Tween-80 (total 0.15 kg) was added to the reaction. The reaction was stirred at 35° C. The reaction was complete within about 5 hours, with a lysine molar conversion rate of about 86%. The enzymatic conversion solution was concentrated to obtain a cadaverine salt solution (about 5%), which was ready for optional further processing.

(3) Enzymatic Conversion of Lysine Fermentation Broth

A 1670 gram of the above-prepared lysine fermentation broth (Example 1) was put into the above-prepared LDC fermentation broth (Example 2) to get 100 L of mixture solution (lysine concentration at 2 g/L). Acetic acid and sodium acetate were added to the reaction to final molar concentrations of 0.2 mol/L, respectively, and Tween-80 (total 0.15 kg) was added to the reaction. The reaction was stirred at 35° C. The reaction was complete within about 8 hours, with a lysine molar conversion rate of about 83%. The enzymatic conversion solution was concentrated to obtain a cadaverine salt solution (about 5%), which was ready for optional further processing.

Example 4

Cadaverine Purification Using Organic Solvent Extraction

A cadaverine chloride enzymatic conversion solution (6% cadaverine) was concentrated on evaporator at a reduced pressure to provide an aqueous cadaverine chloride solution (1,075 L, 1,118 kg, and 9.83% cadaverine). Sodium hydroxide (aq., 30%, 332 L) was added to provide an aqueous cadaverine composition, pH 14. Saturated aqueous butanol solution was added to the above reaction for extraction (400 L). The extraction mixture was stirred/extracted at 50~60° C. for 40 minutes, and sit for 1 hours for the separation of aqueous and organic phases. The aqueous layer was further extracted twice with saturated butanol solution (aq. 400 L) as described above. The organic phases were combined and had a cadaverine concentration of 9%. The combined organic phase was concentrated at 50~60° C. at −0.085 MPa, and further distilled at 80~120° C. at −0.085 MPa for 6 hours to provide a cadaverine recovery yield of 62.35%.

Although the aqueous cadaverine composition was extracted before distillation, significant amount of impurities were still left in the evaporation/distillation composition, which interfered the cadaverine distillation and provided a low cadaverine recovery yield.

Example 5 pH of Some Aqueous Cadaverine Compositions at Room Temperature

The pH of some aqueous cadaverine compositions at room temperature were detected using a pH meter (Table 1).

TABLE 1

The pH of some aqueous cadaverine compositions at room temperature

| Cadaverine Concentration (%) | pH |
|---|---|
| 1 | 12.29 |
| 4.91 | 12.59 |
| 9.9 | 12.74 |
| 19.8 | 12.89 |
| 30 | 13.4 |
| 50 | 14 |

Example 6

Salt-Reduction Processes (I)

A cadaverine sulfate enzymatic conversion solution (1000 g) was concentrated on a rotavap at 50 to 70° C. under −0.09 MPa to a first cadaverine sulfate composition (139.63 g). Another cadaverine sulfate enzymatic conversion solution (1000 g) was concentrated to a second cadaverine sulfate composition (161.00 g) under substantially the same condition. Sodium hydroxide (chemical grade, about 28.3 g) was added to the first cadaverine sulfate composition, and stirred until the pH was greater than 13.3. The mixture was filtered at about 65° C., and the filtered solid was flamed to provide a dry solid (44.38 g) containing 43.87 g sodium sulfate (98.85%). The same process was carried out on the second cadaverine sulfate composition, and the obtained dry solid (42.70 g) contained 42.16 g sodium sulfate (98.94%). Thus, this example showed that according to the methods disclosed herein, salt reduction in a more concentrated cadaverine salt composition was more efficient.

Example 7

Salt-Reduction Processes (II)

A first cadaverine sulfate enzymatic conversion solution (300.74 g, 4.6% cadaverine, 2.83% $SO_4^{2-}$) was concentrated on a rotavap at 50 to 70° C. under −0.09 MPa to a first cadaverine sulfate composition (120.13 g, 11.51% cadaverine, 7.08% $SO_4^{2}$). A second cadaverine sulfate enzymatic conversion solution (300.79 g, 4.6% cadaverine, 2.83% $SO_4^{2-}$) was concentrated to a second cadaverine sulfate composition (79.69 g, 17.36% cadaverine, 10.68% $SO_4^{2-}$) under substantially the same condition. Sodium hydroxide (aq., 18.05 g, 60%, about 1 equivalent) was added to the first cadaverine sulfate composition and filtered at about 65° C. to provide a first aqueous cadaverine composition (9.8% cadaverine, 6.03% $SO_4^{2-}$ in the solution). The same process was carried out on the second cadaverine sulfate composition, and the obtained a second aqueous cadaverine composition (14.90% cadaverine, 5.17% $SO_4^{2-}$ in the solution). Thus, this example showed that according to the methods disclosed herein, salt reduction in a more concentrated cadaverine salt composition was more efficient, and the obtained aqueous cadaverine composition had a lower salt concentration and a higher cadaverine concentration.

Example 8

Solubilities of NaCl and Sodium Sulfate in Aqueous Cadaverine Solutions

At a specific temperature (e.g. 5° C., 18° C., 24° C. or 65° C.), sodium sulfate was added into an aqueous cadaverine solution with a specific cadaverine concentration until a small amount of sodium sulfate was not dissolved. The mixture was stirred for half an hour and allowed to sit for half an hour. The supernatant was removed to detect cadaverine concentration and sulfate concentration. The protocol was repeated for different cadaverine concentrations and/or at different temperatures (Table 2, and FIG. 2).

At a specific temperature (e.g. 5° C., 18° C., 24° C. or 65° C.), NaCl was added into an air-tight system consisting of 50% aqueous cadaverine solution with stirring until a small amount of NaCl was not dissolved. The amount of NaCl added was recorded. Small amounts of water were added just until the insoluble NaCl dissolved completely. The amount of the water added was also recorded. Repeat the addition of NaCl and water steps described above to obtain the solubilities of NaCl at different cadaverine concentrations (Table 3, and FIG. 3).

TABLE 2

Sodium Sulfate Solubilities in Cadaverine Composition (aq.) at 5° C., 18° C., and 65° C.

| T (° C.) | Cadaverine Concentration (%) | Sodium Sulfate Concentration (%) |
|---|---|---|
| 5 | 5.48 | 5.09 |
|   | 9.71 | 3.33 |
|   | 13.46 | 3.31 |
|   | 17.47 | 1.51 |
|   | 24.14 | 0.97 |
| 18 | 5.61 | 10.46 |
|   | 11.48 | 6.41 |
|   | 17.63 | 4.07 |
|   | 24.62 | 2.57 |
|   | 36.32 | 0.93 |
| 65 | 29.90 | 3.56 |
|   | 31.41 | 3.24 |
|   | 38.82 | 0.77 |
|   | 41.06 | 1.05 |
|   | 51.23 | 0.13 |

TABLE 3

Sodium Chloride Solubilities in Cadaverine Composition (aq.) at 24° C.

| T (° C.) | Cadaverine Concentration (%) | Sodium Sulfate Concentration (%) |
|---|---|---|
| 24 | 41.0053 | 9.4428 |
|   | 39.9805 | 10.0113 |
|   | 38.5559 | 11.1982 |
|   | 36.7162 | 12.1321 |
|   | 33.6967 | 13.1604 |

Example 9

Cadaverine Purification of Cadaverine Sulfate Compositions (I)

Cadaverine (52.39 g, 95.00% cadaverine, pH>14.0 at 30° C.) was dissolved in water to provide an aqueous cadaverine solution (250.19 g, pH-12.73 at 30° C.). Sulfuric acid (aq., 163.46 g, 30%) was added to the aqueous cadaverine solution until the pH was about 7 to provide an aqueous cadaverine sulfate solution (413.65 g). The aqueous cadaverine sulfate solution was concentrated on a rotavap at 50 to 70° C. under –0.09 MPa to a concentrated cadaverine sulfate composition having about 30.99% cadaverine. Sodium hydroxide (chemical grade, 41.50 g) was added to the concentrated cadaverine sulfate composition and stirred until the pH was greater than 14.0. The obtained mixture was cooled to about 10° C. and filtered at the same temperature to provide a filtrate of 118.52 g, 37.30% cadaverine. The recovery of cadaverine in the filtrate was about 88.82%. The relatively low recovery was due to the cadaverine left in the filtered wet solid.

Example 10

Cadaverine Purification of Cadaverine Sulfate Compositions (II): with/without Salt Reduction Step b)

A cadaverine sulfate enzymatic conversion solution was concentrated on a rotavap at 50 to 70° C. under –0.09 MPa to a cadaverine sulfate composition (28.52% cadaverine).

Potassium hydroxide (aq., 47.46 g, 60%) was added to a first cadaverine sulfate composition (150 g, 28.52% cadaverine) at 60° C. and stirred at the same temperature to provide a first aqueous cadaverine composition, pH 13.99. The first aqueous cadaverine composition was evaporated under –0.095 MPa in an oil bath until no more evaporation was observed. The temperature of the oil bath increased from 80° C. to 180° C. in 130 min. The distillate collected contained 143.48 g cadaverine (aq., 23.12% cadaverine). The recovery yield of cadaverine was 77.52%.

Potassium hydroxide (aq., 47.46 g, 60%) was added to a second cadaverine sulfate composition (150 g, 28.52% cadaverine) at 60° C. and stirred at the same temperature to provide a second aqueous cadaverine composition, pH 13.98. The second aqueous cadaverine composition was filtered at 60° C. to provide a filtrate of 143.36 g (28.14% cadaverine). The solid obtained from the filtration was weighed while it was wet (51.66 g), washed with saturated sodium sulfate (aq., 26.00 g) and filtered to provide another filtrate of 26.55 g (18.65% cadaverine). The filtrates obtained from both filtrations were combined (169.91 g, containing 45.29 g cadaverine) and evaporated under –0.095 MPa in an oil bath until no more evaporation was observed. The temperature of the oil bath increased from 80° C. to 180° C. in 130 min. The distillate collected contained 197.38 g cadaverine (aq., 20.22% cadaverine). The recovery yield of cadaverine was 93.26%.

Example 11

Cadaverine Purification of Cadaverine Chloride and Cadaverine Sulfate Compositions (1) Cadaverine Purification of a Cadaverine Chloride Composition A cadaverine chloride enzymatic conversion solution (502.23 g, 8.96% cadaverine) was concentrated on a rotavap at 50 to 70° C. under –0.09 MPa to a cadaverine chloride composition (150.00 g).

Sodium hydroxide (38.29 g) was added to the cadaverine chloride composition and stirred to provide a first aqueous cadaverine composition, pH about 14.0. The first aqueous cadaverine composition was filtered at 20° C. to provide a filtrate of 138.35 g (30.18% cadaverine). The solid obtained from the filtration was weighed while it was wet (49.65 g), washed with saturated sodium chloride (aq., 33.00 g) and filtered to provide another filtrate of 43.55 g (11.98% cadaverine). The filtrates obtained from both filtrations were combined (181.90 g) and evaporated under –0.095 MPa in an oil bath until no more evaporation was observed. The temperature of the oil bath increased from 80° C. to 180° C. in 130 min. The distillate collected contained 124.63 g cadaverine with a cadaverine recovery yield of 85.05%.

(2) Cadaverine Purification of a Cadaverine Sulfate Composition

A cadaverine sulfate enzymatic conversion solution (229.00 g, 20.70% cadaverine) was concentrated on a rotavap at 50 to 70° C. under −0.09 MPa to a cadaverine sulfate composition (150.00 g).

Potassium hydroxide (49.52 g) was added to a second cadaverine sulfate composition (150 g, 28.52% cadaverine) at 60° C. and stirred at the same temperature to provide a second aqueous cadaverine composition, pH about 14.0. The second aqueous cadaverine composition was filtered at 40° C. to provide a filtrate of 122.99 g (37.18% cadaverine). The solid obtained from the filtration was weighed while it was wet (72.19 g), washed with saturated sodium sulfate (aq., 39.00 g) and filtered to provide another filtrate of 26.72 g (5.71% cadaverine). The filtrates obtained from both filtrations were combined (149.71 g, containing 31.44% cadaverine) and evaporated under −0.095 MPa in an oil bath until no more evaporation was observed. The temperature of the oil bath increased from 80° C. to 180° C. in 130 min. The distillate collected contained 121.13 g cadaverine with a cadaverine recovery yield of 95.78%.

The invention claimed is:

1. A method for the purification of cadaverine from an aqueous cadaverine salt composition without organic solvent extraction, comprising:
   a) adjusting the pH an aqueous cadaverine salt composition to a pH of at least about 12 to provide a first composition comprising an aqueous cadaverine composition having a pH of at least about 12 and a solid composition;
   b) removing the solid composition from the first composition of step a) without organic solvent extraction to provide an aqueous cadaverine composition; and
   c) distilling or evaporating the aqueous cadaverine composition without organic solvent extraction to provide purified cadaverine.

2. A method for a production of purified bio-based cadaverine without organic solvent extraction comprising:
   a-1) providing an aqueous cadaverine salt composition comprising a cadaverine production composition, wherein the cadaverine production composition is obtained from a bio-based cadaverine production process;
   a) adjusting the pH of the aqueous cadaverine salt composition to a pH of at least about 12 to provide a first composition comprising an aqueous cadaverine composition having a pH of at least about 12 and a solid composition;
   b) removing the solid composition from the first composition of step a) without organic solvent extraction to provide an aqueous cadaverine composition; and
   c) distilling or evaporating the aqueous cadaverine composition without organic solvent extraction to provide purified bio-based cadaverine.

3. The method of claim 1, further comprising:
   a-1) concentrating the aqueous cadaverine salt composition before the addition of the one or more bases; and/or
   a-2) concentrating the aqueous cadaverine salt composition/base reaction after the addition of the one or more bases; and/or
   a-3) concentrating the aqueous cadaverine salt composition/base reaction during the addition of the one or more bases.

4. The method of claim 3, wherein the cadaverine concentration of the aqueous cadaverine composition of step a) is about 5% or higher.

5. The method of claim 3, wherein the cadaverine concentration of the aqueous cadaverine composition of step a) is about 20% or higher.

6. The method of claim 1, wherein step b) comprises:
   b-1) filtering/centrifuging the first composition to provide a solid and a filtrate/supernatant;
   b-2) rinsing the solid with an aqueous salt solution and filtering/centrifuging the obtained mixture to provide another solid and another filtrate/supernatant;
   b-3) optionally repeating step b-2) until the solid obtained is substantially free of cadaverine; and
   b-4) combining the filtrates/supernatants obtained from steps b-1), b-2) and b-3) to provide the aqueous cadaverine composition to be further processed in step c).

7. The method of claim 1, wherein the acid anion content of the aqueous cadaverine composition is no more than about 50% of that of the aqueous cadaverine salt composition.

8. The method of claim 1, wherein the acid anion content of the aqueous cadaverine composition is no more than about 70% of that of the aqueous cadaverine salt composition.

9. The method of claim 1, wherein the aqueous cadaverine salt composition comprises one or more cadaverine salts selected from the group consisting of cadaverine sulfate, cadaverine chloride, cadaverine carbonate, cadaverine phosphate and any combinations thereof.

10. The method of claim 1, wherein the aqueous cadaverine salt composition has a pH of about 11 or lower.

11. The method of claim 1, wherein the pH of the first composition of step a) is about 13.3 or higher.

12. The method of claim 1, wherein step a) comprises adding an inorganic base composition into the aqueous cadaverine salt composition, wherein the inorganic base composition comprises one or more inorganic bases selected from the group consisting of alkaline metal hydroxides, alkaline earth metal hydroxides, and basic salts thereof.

13. The method of claim 12, wherein the one or more inorganic bases are selected from the group consisting of NaOH, KOH, $Na_3PO_4$, $Na_2CO_3$, and any combinations thereof.

14. The method of claim 1, wherein the aqueous cadaverine composition obtained from step b) is distilled at a reduced pressure or ambient pressure.

* * * * *